United States Patent [19]

Nakajima et al.

[11] Patent Number: 5,034,321

[45] Date of Patent: Jul. 23, 1991

[54] METHOD FOR THE PRODUCTION OF LIPIDS CONTAINING BIS-HOMO-γ-LINOLENIC ACID

[75] Inventors: Toshiaki Nakajima; Toshio Sano, both of Sodegaura, Japan

[73] Assignee: Idemitsu Petrochemical Co., Ltd., Tokyo, Japan

[21] Appl. No.: 226,992

[22] Filed: Aug. 1, 1988

[30] Foreign Application Priority Data

Aug. 19, 1987 [JP] Japan .................................. 62-204160
Aug. 19, 1987 [JP] Japan .................................. 62-204161

[51] Int. Cl.$^5$ .......................... C12P 7/64; C12P 7/62; C12N 1/38
[52] U.S. Cl. ................................... 435/134; 435/135; 435/244; 435/911
[58] Field of Search ................ 435/134, 135, 244, 911

[56] References Cited

U.S. PATENT DOCUMENTS 4,783,408 11/1988 Suzuki et al. ...................... 435/134

FOREIGN PATENT DOCUMENTS 0252716 1/1988 European Pat. Off. ............ 435/134
0276541 8/1988 European Pat. Off. ............ 435/134
102688-A 7/1988 Japan .

OTHER PUBLICATIONS

Miura et al, "Fatty Acid and Lipid Compositions of Conidiobolus", *J. Appl. Bacteriol.,* 1983, 54(1), pp. 85–90.
ATCC Catalogue of Fungi, 1987, pp. 111–114.
Canadian Journal of Microbiology, vol. 17, 1971, pp. 1115–1118; D. Tyrrell: "The Fatty Acid Composition of Some Entomophthoraceae. III".
Chemical Abstracts, vol. 105, No. 25, Dec. 22, 1986, p. 625, No. 224603y, & JP-A-61 177 990 (Harima Chem.).

*Primary Examiner*—Douglas W. Robinson
*Assistant Examiner*—Irene Marx
*Attorney, Agent, or Firm*—Frishauf, Holtz, Goodman & Woodward

[57] ABSTRACT

Method for the production of lipds containing bis-homo-γ-linolenic acid and/or arachidonic acid using microorganisms belonging to a genus Conidiobolus and capable of producing the lipids. The microorganisms are cultured on a medium containing an unsaturated fatty acid as a carbon source. The unsaturated fatty acid may be supplied as an additional carbon source in the course of culture. Preferably, the unsaturated fatty acid has 18 carbon atoms and 1 to 3 double bonds.

16 Claims, No Drawings

METHOD FOR THE PRODUCTION OF LIPIDS CONTAINING BIS-HOMO-γ-LINOLENIC ACID

BACKGROUND OF THE INVENTION

The present invention relates to a method for producing lipids containing bis-homo-γ-linolenic acid and/or arachidonic acid with improved efficiency.

For the production of bis-homo-γ-linolenic acid or arachidonic acid useful as medicines and biochemical reagents, there have been known methods for preparing arachidonic acid using microorganisms belonging to genera Penicillium, Cladosporium, Mucor, Fusarium, Hormodendrum, Aspergillus and Rhodotorula (Japanese Patent Kokai Koho 52-64484) and employing *Mortierella elongata* (H. YAMADA, et al, "Agric. Biol. Chem.", 51, 785, 1987). However, such methods have been disadvantageous in that the amount of the end product produced is small.

It has also been known that microorganisms belonging to a genus Conidiobolus produce bis-homo-γ-linolenic acid and arachidonic acid (D. Tyrell, "Can. J. Microbiol.", 17, 1115, 1971). However, such a method is also poor in the productivity of the end products. Further, proposals have been made of a method for mass-producing arachidonic acid employing Conidiobolus microbes and using glucose as a carbon source (Sakuzo Fukui, et al, "Proceedings of Japan Agricultural Chemistry Society", pp. 156, 1987). A problem with this is also that the amount of the end product to be produced is less than satisfactory.

SUMMARY OF THE INVENTION

As a result of studies made to improve the productivity of lipids containing bis-homo-γ-linolenic acid and arachidonic acid, it has now been found that the object is achieved by using a culture medium containing a carbon source containing an unsaturated fatty acid as an essential component. The present invention has been accomplished on the basis of such findings.

More specifically, according to one aspect of the present invention, there is provided a method for the production of lipids containing bis-homo-γ-linolenic acid and/or arachidonic acid, which is characterized in that a microorganism belonging to a genus Conidiobolus and capable of producing a lipid containing bis-homo-γ-linolenic acid and/or arachidonic acid is cultured on a carbon source-containing medium, during which an unsaturated fatty acid is supplied as an additional carbon source, and bis-homo-γ-linolenic acid and/or arachidonic acid are collected from the thus cultured mass.

According to another aspect of the present invention, there is provided a method for the production of lipids containing bis-homo-γ-linolenic acid and/or arachidonic acid, which is characterized in that a microorganism belonging to a genus Conidiobolus and capable of producing lipids containing bis-homo-γ-linolenic acid and/or arachidonic acid is cultured on a medium containing an unsaturated fatty acid as a carbon source, and bis-homo-γ-linolenic acid and/or arachidonic acid are collected from the thus cultured mass.

DETAILED DESCRIPTION OF THE INVENTION

The microorganisms belonging to the genus Conidiobolus and capable of producing bis-homo-γ-linolenic acid and/or arachidonic acid may include, for instance, *Conidiobolus heterosporus* ATCC 12941, *Conidiobolus globuliferus* CBS 218/64 and *Conidiobolus nanodes* CBS 183/62 (CBS depository is Centraalbureau Voor Schimmelcultures, Baarn, the Netherlands).

The media used for culturing the aforesaid microorganisms according to the first aspect of the present invention may contain carbon sources, nitrogen sources, inorganic salts and so on. As the carbon sources, use may be made of carbohydrates such as glucose, starch and blackstrap molasses as well as unsaturated fatty acids which may be used alone or in combination with such substances. The nitrogen sources should preferably contain organic nitrogen, and may be exemplified by yeast extracts, peptone, malt extracts and corn steep liquor by way of example alone. The inorganic salts used may include magnesium salts (e.g., $MgSO_4 \cdot 7H_2O$), potassium phosphate ($KH_2PO_4$), iron salts ($FeSO_4 \cdot 7H_2O$), zinc salts ($ZnSO_4$) and so on. If required, trace elements and nutrient sources suitable for the growth of microorganisms may be additionally supplied.

The amount of the carbon source to be added may suitably be in a range of 2 to 5% by volume of the medium. Usually, culture may be carried out in the form of, e.g., shaken culture or aeration-agitation culture on liquid media. The culture conditions regarding temperature, time, etc. may be such that the amount of the end lipids to be produced is increased with the nature of the microorganisms, etc. in mind. Usually, culture is carried out at 15° to 40° C., preferably 20° to 30° C. for 2 to 7 days, preferably 3 to 5 days.

In order to increase the amount of the end lipids to be produced, it is essentially required in the present invention that the microorganisms be cultured on the aforesaid media by supplying thereto an unsaturated fatty acid as an additional carbon source in the course of culture. By the unsaturated fatty acid is preferably meant an unsaturated fatty acid having 18 carbon atoms and one to three double bonds such as, for instance, oils and fats having a high content of linoleic acid, e.g., safflower oil, sunflower oil; Oenothera tetraptera oil that is γ-linolenic acid-containing oils and fats; microbial oils and fats extracted from moulds belonging to genera Mortierella, Mucor, Cunninghamella and the like; and so on. Free acids such as linoleic acid and γ-linolenic acid or esters may also be used. The amount, time, etc. of the addition of the unsaturated fatty acid may be determined such that the amount of the end lipids to be produced is increased, while taking the growth of microbes, etc. into consideration. Usually, 0.5 to 5% by volume of the unsaturated fatty acid, calculated as such, may be added in one to several portions. Although the time of addition is not critical, the unsaturated fatty acid may preferably be added within three days after the beginning of culture.

In the second aspect of the present invention, it is essentially required that the media used for culturing the microorganisms as stated above contain an unsaturated fatty acid as a carbon source. The unsaturated fatty acids used to this end are the same as already mentioned. Preferably, the unsaturated fatty acid acting as the carbon source is added to the media in a proportion of 0.5 to 10% by volume. As the carbon sources, carbohydrates such as glucose, starch and blackstrap molasses may be used in combination with said unsaturated fatty acid. In this case, the carbohydrates may suitably be added in an amount of 2 to 5% by volume.

It is noted that the nitrogen source, inorganic salts and the like to be added to the media may be the same as already mentioned. It is also noted that the conditions for culturing the aforesaid microorganisms inoculated to the media may be the same as already mentioned.

After the end lipids have been produced in this manner, they are collected from the cultured mass. The lipids containing bis-homo-γ-linolenic acid and/or arachidoic acid may be collected directly from the cultured mass; however, it is preferred that the biomass is separated from the cultured mass and the end lipids are collected from the thus obtained biomass, since the cultured mass contains the oils and fats added as the carbon source. In this case, the bis-homo-γ-linolenic acid and/or arachidonic acid may be separated and refined in conventional manners inclusive of, e.g., solvent extraction and chromatography.

According to the present invention, the yields of γ-linolenic acid and arachidonic acid are further increased by adding an unsaturated fatty acid as the carbon source in the course of culture or from the outset, when comparing with the conventional culture methods using carbohydrates as the carbon source. Thus, lipids containing bis-homo-γ-linolenic acid and arachidonic acid can be mass-produced with improved efficiency. Such effects become marked especially when sunflower oil or γ-linolenic acid-containing oils are used as the unsaturated fatty acid-containing oils. The obtained bis-mono-γ-linolenic acid and arachidonic acid are useful for medicines and biochemical reagents.

The present invention will be explained specifically but not exclusively with reference to the following examples.

EXAMPLE 1

One hundred (100) ml of a medium having a composition as specified in Table 1 and containing 30 g/l of glucose were put in each of seven Erlenmeyer flasks of 500 ml, and were inoculated with *Conidiobolus heterosporus* ATCC. 12941 for three-day shaken culture of 20° C.

TABLE 1

| Composition of Culture Medium | |
|---|---|
| $KH_2PO_4$ | 3 g |
| $MgSO_4$ | 1 g |
| Peptone | 10 g |
| Yeast Extract | 5 g |
| $FeSO_4$ | 0.01 g |
| Distilled Water | 1 liter |

After the completion of culture, triolein (69% oleic acid and 11% linoleic acid), sunflower oil (19% oleic acid and 69% linoleic acid), linseed oil (15% oleic acid, 16% linoleic acid and 60% α-linolenic acid), an oil containing 8% of γ-linolenic acid (oils and fats extracted from Mortierella moulds; 43% oleic acid, 12% linoleic acid and 8% γ-linoleic acid), an oil containing 16% of γ-linolenic acid (oils and fats extracted from Mucor moulds; 40% oleic acid, 10% linoleic acid and 16% γ-linolenic acid) and an oil containing 32% of γ-linolenic acid (oils and fats extracted from Mucor moulds; 28% oleic acid, 16% linoleic acid and 32% γ-linolenic acid) were added to the media in a proportion of 1% by volume per 1 liter, and were further cultured at 20° C. for two days. For the purpose of control, 10 g/l of glucose were added to the remaining medium and cultured in a similar manner as above.

After the completion of culture, the biomasses were collected by cetrifugation, washing with a phosphate buffer (pH 7.0) and suction filtration. The collected biomasses were put in a stainless cup and crushed with glass beads, methanol and chloroform by means of a homogenizer to extract lipids therefrom. The extracted lipids were methyl-esterified and gaschromatographed to analyze the composition of the fatty acids contained therein. The results are summarized in Table 2.

TABLE 2

Yields of Biomasses, Bis-Homo-γ-Linolenic Acid and Arachidonic Acid When Performing Three-day Culture at 20° C. Using Glucose as Carbon Source and Further Two-day Culture with Oils and Fats

| Carbon Source | | Yield of Biomasses (g/l) | Content of Oils and Fats (%) | Yield of Oils and Fats (g/l) | Content of Bis-Homo-γ-Linolenic Acid (%) | Yield of Bis-Homo-γ-Linolenic Acid (g/l) | Content of Arachidonic Acid (%) | Yield of Arachidonic Acid (g/l) |
|---|---|---|---|---|---|---|---|---|
| Triolein | | 21.6 | 38.0 | 8.21 | 0.68 | 0.056 | 8.18 | 0.67 |
| Sunflower Oil | | 22.7 | 44.4 | 10.1 | 1.38 | 0.139 | 7.45 | 0.75 |
| Linseed Oil | | 20.8 | 45.3 | 9.44 | 0.28 | 0.026 | 6.98 | 0.66 |
| γ-Linolenic | 8% | 20.3 | 45.6 | 9.26 | 1.63 | 0.151 | 11.02 | 1.02 |
| Acid-Contain- | 16% | 18.2 | 40.6 | 7.39 | 2.15 | 0.159 | 12.65 | 0.94 |
| ing Oils | 32% | 19.6 | 42.5 | 8.33 | 2.22 | 0.185 | 12.98 | 1.08 |
| Control | | 12.6 | 22.8 | 2.87 | 0.79 | 0.022 | 15.20 | 0.44 |

Control: Culturing in a medium containing 30 g/l of glucose as the carbon source and then 10 g/l of glucose was added to the medium.

Evidently, Table 2 indicates that the addition of triolein, sunflower oil and γ-linolenic acid-containing oils resulted in a 2.5 to 10-fold increase in the yield of bis-homo-γ-linolenic acid in comparison with the control. The yield of arachidonic acid was approximately doubled.

It is appreciated that bis-homo-γ-linolenic acid and arachidonic acid were identified in the following manners. (1) Capillary gas-chromatography (PEG 20 M column) indicated that the obtained bis-homo-γ-linolenic acid and arachidonic acid coincided with the standard samples in retention time. Capillary gas-chromatography of a mixture of the samples with the lipids extracted from the biomasses and methyl-esterified indicated that there were increases in the peaks of the fractions of bis-homo-γ-linolenic acid and arachidonic acid. (2) The triene and tetraene fractions were separated by silver nitrate-impregnated thin layer chromatography, and were then oxidized by the osmium oxidation method. Thereafter, they were trimethylsilyl-etherified and identified by capillary gas-mass chromatographic spectra.

EXAMPLE 2

This example was performed in a similar manner as described in Example 1, except that after the completion of the first culture, ethyl ester of various fatty acids was added to the media in a proportion of 1% by volume per 1 liter, and further cultured at 20° C. for two days. The results are set out in Table 3.

TABLE 3

Yields of Biomasses, Bis-Homo-γ-Linolenic Acid and Arachidonic Acid When Ethyl Esters Were Added

| Carbon Source | Yield of Biomasses (g/l) | Content of Oils and Fats (%) | Yield of Oils and Fats (g/l) | Content of Bis-Homo-γ-Linolenic Acid (%) | Yield of Bis-Homo-γ-Linolenic Acid (g/l) | Content of Arachidonic Acid (%) | Yield of Arachidonic Acid (g/l) |
| --- | --- | --- | --- | --- | --- | --- | --- |
| Ethyl Oleate | 22.1 | 32.3 | 7.1 | 0.46 | 0.033 | 9.7 | 0.69 |
| Ethyl Linoleate | 18.1 | 31.0 | 7.0 | 1.29 | 0.073 | 9.9 | 0.56 |
| Ethyl α-Linolenate | 18.2 | 26.4 | 4.8 | 0.15 | 0.008 | 10.4 | 0.50 |
| Ethyl γ-Linolenate | 20.6 | 26.8 | 5.5 | 4.11 | 0.227 | 14.9 | 0.82 |

Evidently, Table 3 indicates that the addition of the ethyl esters of oleic acid, linoleic acid and γ-linolenic acid resulted in 1.5 to 10-fold increases in the yield of bis-homo-γ-linolenic acid. The addition of the ethyl ester of γ-linolenic acid also gave rise to an increase in the yield of arachidonic acid.

EXAMPLE 3

Five (5) liters of a medium were prepared by adding 30 g/l of glucose to the medium shown in Table 1, and were placed in a 10-liter jar fermenter, in which it was sterilized at 121° C. for 15 minutes. That medium was inoculated with *Conidiobolus heterosporus* ATCC. 12941 precultured on 600 ml of a similar medium, which was then subjected to aeration-agitation culture at 20° C. for three days. After the completion of culture, 150 g of a γ-linolenic acid-containing oil (8%) were put into the jar fermenter for further two-day culture.

After the completion of culture, the biomass was collected, dehydrated with ethanol and dried. Afterwards, the lipid was extracted from the biomass with n-hexane, using a ball mill. The amount of the lipid extracted with n-hexane was 110 grams. Compositional analysis of the fatty acids in such lipid indicated that it contained 3% of bis-homo-γ-linolenic acid and 10% of arachidonic acid. The yields of bis-homo-γ-linolenic acid and arachidonic acid were 3.3 grams and 11 grams, respectively.

EXAMPLE 4

This example was performed in a similar manner as stated in Example 1, except that the arachidonic acid-producing microbes shown in Table 4 were used, and they were cultured on glucose-containing media at 20° C. for three days, followed by the addition of a γ-linolenic acid-containing oil (8%) in a proportion of 1% by volume per 1 liter medium. The results are given in Table 4.

TABLE 4

| | Yield of Oils and Fats (g/l) | Yield of Bis-Homo-γ-Linolenic Acid (g/l) | Yield of Arachidonic Acid (g/l) |
| --- | --- | --- | --- |
| *Conidiobolus heterosporus* ATCC 12941 | 9.3 (4.0) | 0.15 (0.05) | 1.0 (0.53) |
| *Conidiobolus globuliferous* CBS 218/64 | 3.43 (1.5) | 0.02 (0.01) | 0.4 (0.12) |
| *Conidiobolus nanodes* CBS 183/62 | 7.5 (2.3) | 0.16 (0.06) | 1.41 (0.19) |

*Bracketed figures are those obtained by culturing on the control medium.

EXAMPLE 5

A γ-linolenic acid-containing oil (oils and fats from Mortierella moulds; 43% oleic acid, 11% linoleic acid and 8% γ-linolenic acid) was added to the medium shown in Table 1, in the proportions of 1% by volume, 2% by volume, 3% by volume and 5% by volume, thereby preparing four media. One hundred (100) ml of each medium were put in a 500-ml Erlenmeyer flask, and were inoculated with *Conidiobolus heterosporus* ATCC 12941, which was subjected to shaken culture at 30° C. for three days.

After the completion of culture, the biomasses were collected by centrifugation, washing with a phosphate buffer (pH 7.0) and suction filtration. The collected biomasses were put in a stainless cup and crushed with glass beads, methanol and chlororform by means of a homogenizer to extract lipids therefrom. The extracted lipids were methyl-esterified and gas-chromatographed to analyze the composition of the fatty acids contained therein. The results are summarized in Table 5.

TABLE 5

Relations Between The Amount of Oils and Fats As Carbon Source and The Yields of Biomasses, Bis-Homo-γ-Linolenic Acid and Arachidonic Acid

| Amount of γ-Linolenic Acid-Containing Oils | Yield of Biomasses (g/l) | Content of Oils and Fats (%) | Yield of Oils and Fats (g/l) | Content of Bis-Homo-γ-Linolenic Acid (%) | Yield of Bis-Homo-γ-Linolenic Acid (g/l) | Content of Arachidonic Acid (%) | Yield of Arachidonic Acid (g/l) |
| --- | --- | --- | --- | --- | --- | --- | --- |
| 1 vol % | 12.7 | 33.0 | 4.19 | 2.68 | 0.12 | 16.1 | 0.67 |
| 2 vol % | 20.5 | 43.2 | 8.87 | 2.80 | 0.25 | 11.8 | 1.05 |
| 3 vol % | 21.7 | 45.9 | 9.97 | 3.10 | 0.31 | 10.5 | 1.05 |

TABLE 5-continued

Relations Between The Amount of Oils and Fats
As Carbon Source and The Yields of Biomasses,
Bis-Homo-γ-Linolenic Acid and Arachidonic Acid

| Amount of γ-Linolenic Acid-Containing Oils | Yield of Biomasses (g/l) | Content of Oils and Fats (%) | Yield of Oils and Fats (g/l) | Content of Bis-Homo-γ-Linolenic Acid (%) | Yield of Bis-Homo-γ-Linolenic Acid (g/l) | Content of Arachidonic Acid (%) | Yield of Arachidonic Acid (g/l) |
| --- | --- | --- | --- | --- | --- | --- | --- |
| 5 vol % | 20.7 | 44.1 | 9.12 | 3.20 | 0.29 | 9.7 | 0.88 |

From Table 5, it is obvious that the yield of the biomass reached approximately an optimum at the addition of 3% by volume of the oils and fats to the medium. It is also evident that the yields of bis-homo-γ-linolenic acid and arachidonic acid reached a substantial high, when the amount of the oils and fats added was 3% by volume.

It is appreciated that bis-homo-γ-linolenic acid and arachidonic acid were identified in the following manners. (1) Capillary gas-chromatography (PEG 20 M column) indicated that the obtained bis-homo-γ-linolenic acid and arachidonic acid coincided with the standard samples in retention time. Capillary gas-chromatography of a mixture of the samples with the lipids extracted from the biomasses and methyl-esterified indicated that there were increases in the peaks of the fractions of bis-homo-γ-linolenic acid and arachidonic acid. (2) The triene and tetraene fractions were separated by silver nitrate-impregnated thin layer chromatography, and were then oxidized by the osmium oxidation method. Thereafter, they were trimethylsilyl-etherified and identified by capillary gas-mass chromatographic spectra.

COMPARATIVE EXAMPLE 1

In this example, the inoculation and culture of microorganisms and the analysis of the produced lipids were performed in a similar manner as described in Example 5, except that in place of the media used in the example, use was made of those obtained by 0 g/l, 30 g/l, 50 g/l and 70 g/l of glucose to the medium shown in Table 1. The results are summed up in Table 6.

TABLE 6

Yields of Biomasses, Bis-Homo-γ-Linolenic Acid and
Arachidonic Acid After Three-day Culture at 20° C.
Using Glucose as Carbon Source

| Amount of Glucose (g/l) | Yield of Biomasses (g/l) | Content of Oils and Fats (%) | Yield of Oils and Fats (g/l) | Content of Bis-Homo-γ-Linolenic Acid (%) | Yield of Bis-Homo-γ-Linolenic Acid (g/l) | Content of Arachidonic Acid (%) | Yield of Arachidonic Acid (g/l) |
| --- | --- | --- | --- | --- | --- | --- | --- |
| 0 | 7.1 | 15.6 | 1.1 | 0.46 | 0.005 | 15.1 | 0.17 |
| 30 | 18.1 | 29.6 | 5.4 | 0.44 | 0.024 | 11.7 | 1.63 |
| 50 | 18.1 | 24.5 | 4.4 | 0.50 | 0.023 | 10.8 | 0.47 |
| 70 | 17.3 | 17.7 | 3.1 | 0.36 | 0.011 | 9.7 | 0.30 |

Evidently, Table 6 indicates that the addition of 30 g/l of glucose gave rise to the highest biomass yield substantially similar to that achieved by the addition of 50 g/l of glucose.

EXAMPLE 6

The inoculation and culture of microbes and the analysis of the produced lipids were performed in a similar manner as described in Example 5, except that in place of the medium used in Example 5, medium obtained by adding to one liter of the medium shown in Table 1, 3% by volume of a lipid selected from the group consisting of triolein (69% oleic acid and 11% linoleic acid), sunflower oil (19% oleic acid and 69 % linoleic acid), linseed oil (15% oleic acid, 16% linoleic acid and 60% γ-linoleic acid), an oil containing 8% of γ-linolenic acid (oils and fats extracted from Mortierella moulds; 43% oleic acid, 12% linoleic acid and 8% γ-linolenic acid), an oil containing 16% of γ-linolenic acid (oils and fats extracted from Mucor moulds; 40% oleic acid, 10% linoleic acid and 16% γ-linolenic acid) and an oil containing 32% of 65-linolenic acid (oils and fats extracted from Mucor moulds; 28% oleic acid, 16% linoleic acid and 32% γ-linolenic acid) was used, and a culture temperature of 20° C. was applied. The results are set out in Table 7.

TABLE 7

Yields of Biomasses, Bis-Homo-γ-Linolenic Acid
and Arachidonic Acid When Performing Three-day
Culture at 20° C. Using Oils and Fats as Carbon Source

| Carbon Source | | Yield of Biomasses (g/l) | Content of Oils and Fats (%) | Yield of Oils and Fats (g/l) | Content of Bis-Homo-γ-Linolenic Acid (%) | Yield of Bis-Homo-γ-Linolenic Acid (g/l) | Content of Arachidonic Acid (%) | Yield of Arachidonic Acid (g/l) |
| --- | --- | --- | --- | --- | --- | --- | --- | --- |
| Triolein | | 27.5 | 45.5 | 12.5 | 0.95 | 0.12 | 5.0 | 0.63 |
| Sunflower Oil | | 27.8 | 41.0 | 11.4 | 2.28 | 0.26 | 5.1 | 0.63 |
| Linseed Oil | | 25.9 | 44.0 | 11.4 | 0.41 | 0.05 | 5.0 | 0.57 |
| γ-Linolenic Acid-Containing Oils | 8% | 25.7 | 43.4 | 11.1 | 2.60 | 0.29 | 11.3 | 1.25 |
| | 16% | 23.8 | 42.0 | 10.5 | 3.47 | 0.36 | 11.4 | 1.20 |
| | 32% | 22.6 | 44.2 | 10.0 | 5.84 | 0.58 | 11.2 | 1.11 |
| Control | | 19.0 | 20.0 | 3.8 | 1.16 | 0.04 | 14.6 | 0.55 |

Control: 30 g/l of glucose was used as the carbon source.

Evidently, Table 7 indicates that the use of triolein, sunflower oil and γ-linolenic acid-containing oils gave rise to a 2 to 11-fold increase in the yield of bis-homo-γ- linolenic acid, when comparing with the control wherein culture was performed with 30 g/l of glucose. With the γ-linolenic acid-containing oils, the yield of arachidonic acid was approximately doubled.

EXAMPLE 7

The inoculation and culture of microbes and the analysis of the lipids were performed in a similar manner as described in Example 6, except that sunflower oil and oils containing 8%, 16% and 32% of γ-linolenic acid were used as the oils and fats, and a culture temperature of 30° C. was applied. The results are summarized in Table 8.

contained 6% of bis-homo-γ-linolenic acid and 12.5% of arachidonic acid. The yields of bis-homo-γ-linolenic acid and arachidonic acid were 7.5 grams and 15.6 grams, respectively.

EXAMPLE 9

Media were prepared by adding 30 g/l of glucose or 3% by volume of a γ-linolenic acid-containing oil (8%) to the medium shown in Table 1, the former called the glucose medium and the latter the γ-linolenic acid medium. One hundred (100) ml of each medium were placed in a 500-ml Erlenmeyer flask, and were inoculated with the arachidonic acid-producing microbes

TABLE 8

Yields of Biomasses, Bis-Homo-γ-Linolenic Acid and Arachidonic Acid When Performing Three-day Culture at 30° C. Using Oils and Fats as Carbon Source

| Carbon Source | | Yield of Biomasses (g/l) | Content of Oils and Fats (%) | Yield of Oils and Fats (g/l) | Content of Bis-Homo-γ-Linolenic Acid (%) | Yield of Bis-Homo-γ-Linolenic Acid (g/l) | Content of Arachidonic Acid (%) | Yield of Arachidonic Acid (g/l) |
|---|---|---|---|---|---|---|---|---|
| Sunflower Oil | | 26.0 | 44.7 | 11.6 | 1.70 | 0.19 | 4.81 | 0.56 |
| γ-Linolenic | 8% | 21.7 | 45.9 | 10.0 | 3.10 | 0.31 | 10.5 | 1.05 |
| Acid-Contain- | 16% | 22.5 | 40.3 | 9.1 | 3.60 | 0.33 | 10.2 | 0.93 |
| ing Oils | 32% | 21.0 | 39.0 | 8.2 | 4.80 | 0.39 | 11.0 | 0.90 |
| Control | | 18.1 | 29.6 | 5.4 | 0.44 | 0.02 | 11.7 | 0.63 |

Control: 30 g/l of glucose was used as the carbon source.

Evidently, Table 8 indicates that the use of sunflower oil and γ-linolenic acid-containing oils gave rise to a 10 to 20-fold increase in the yield of bis-homo-γ-linolenic acid, when comparing with the control wherein culture was performed with 30 g/l of glucose. With the γ-linoshown in Table 9, which were then subjected to shaken culture at 20° C. for three days. After the completion of the shaken culture, the formed lipids were analyzed in a similar manner as in Example 5. The results are summarized in Table 9.

TABLE 9

Yields of Bis-Homo-γ-Linolenic Acid and Arachidonic Acid by Microbes Capable of Producing Arachidonic Acid

| | Yield of Oils and Fats (g/l) | | Yield of Bis-Homo-γ-Linolenic Acid (g/l) | | Yield of Arachidonic Acid (g/l) | |
|---|---|---|---|---|---|---|
| Microbes | Glucose Medium | γ-Linolenic Acid Medium | Glucose Medium | γ-Linolenic Acid Medium | Glucose Medium | γ-Linolenic Acid Medium |
| Conidiobolus heterosporus ATCC 12941 | 4.0 | 11.1 | 0.05 | 0.30 | 0.58 | 1.25 |
| Conidiobolus firmipilleus ATCC 12242 | 2.3 | 2.9 | <0.01 | 0.02 | 0.12 | 0.17 |
| Conidiobolus globuliferous CBS 218/64 | 1.5 | 1.9 | 0.01 | 0.06 | 0.12 | 0.20 |
| Conidiobolus nanodes CBS 183/62 | 2.3 | 7.5 | 0.06 | 0.12 | 0.19 | 1.10 | lenic acid-containing oils, the yield of arachidonic acid was also increased about 1.5-fold.

EXAMPLE 8

Two hundred and fifty (250) grams of a γ-linolenic acid-containing oil (16%) were added to 5 liters of the medium shown in Table 1, which was then placed in a 10-liter jar fermenter, and was sterilized at 121° C. for 15 minutes. That medium was inoculated with *Conidiobolus heterosporus* ATCC 12941 pre-cultured on 600 ml of a medium prepared by adding 30 g/l of glucose to the medium shown in Table 1, which was then subjected to aeration-agitation culture at 20° C. for five days.

After the completion of culture, the biomass was collected, dehydrated with ethanol and dried. Afterwards, the lipid was extracted from the biomass with hexane, using a ball mill. The amount of the lipid extracted with hexane was 125 grams. Compositional analysis of the fatty acids in such lipid indicated that is Evidently, Table 9 indicates that all the microbes give rise to a larger increase in the yields of the oils and fats, γ-linolenic acid and arachidonic acid on the γ-linolenic acid medium than on the glucose medium, and the culture method making use of γ-linolenic acid is effective.

What is claimed is:

1. A method for the production of lipids containing bis-homo-γ-linolenic acid, which comprises
   culturing a microorganism selected from the group consisting of *Conidiobolus heterosporus* ATCC 12941, *Conidiobolus firmipilleus* ATCC 12242, *Conidiobolus globuliferus* CBS 218/64 and *Conidiobolus nanodes,* CBS 183/62, on a carbon source-containing medium,
   supplying an unsaturated fatty acid selected from the group consisting of γ-linolenic acid-containing oils and fats, γ-linolenic acid, an ester of γ-linolenic acid and a mixture thereof, as an additional carbon source in the course of culturing, and then collecting lipids containing bis-homo-γ-linolenic acid from the thus cultured biomass.

2. A method for the production of lipids containing bis-homo-γ-linolenic acid which comprises culturing a microorganism selected from the group consisting of *Conidiobolus heterosporus,* ATCC 12941 *Conidiobolus firmipilleus,* ATCC 12242 *Conidiobolus globuliferus,* CBS 218/64 and *Conidiobolus nanodes,* CBS 183/62, on a medium containing an unsaturated fatty acid selected from the group consisting of γ-linolenic acid-containing oils and fats, γ-linolenic acid, an ester of γ-linolenic acid and a mixture thereof, and then collecting lipids containing bis-homo-γ-linolenic acid from the thus cultured biomass.

3. The method of claim 1, wherein the microorganism is said *Conidiobolus firmipilleus* ATCC 12242.

4. The method of claim 1, wherein the microorganism is said *Conidiobolus globuliferus* CBS 218/64.

5. The method of claim 2, wherein the microorganism is said *Conidiobolus firmipilleus* ATCC 12242.

6. The method of claim 2, wherein the microorganism is said *Conidiobolus globuliferus* CBS 218/64.

7. The method of claim 1, wherein the microorganism is said *Conidiobolus firmipilleus* ATCC 12242 or *Conidiobolus globuliferus* CBS 218/64.

8. The method of claim 2, wherein the microorganism is said *Conidiobolus firmipilleus* ATCC 12242 or *Conidiobolus globuliferus* CBS 218/64.

9. The method of claim 1, wherein the culturing is conducted at a temperature of 15° to 40° C. for 2 to 7 days.

10. The method of claim 2, wherein the culturing is conducted at a temperature of 15° to 40° C. for 2 to 7 days.

11. The method of claim 1, wherein the γ-linolenic acid-containing oil is Oenothera tetraptera oil.

12. The method of claim 2, wherein the γ-linolenic acid-containing oil is Oenothera tetraptera oil.

13. The method of claim 1, wherein 0.5 to 5% by volume of said unsaturated fatty acid is added.

14. The method of claim 1, wherein the microorganism is *C. heterosporus* ATCC 12941 or *C. nanodes* CBS 183/62.

15. The method of claim 2, wherein the medium contains 0.5 to 5% by volume of said unsaturated fatty acid.

16. The method of claim 2, wherein the microorganism is *C. heterosporus* ATCC 12941 or *C. nanodes* CBS 183/62.

* * * * *